United States Patent
Ujihara et al.

(10) Patent No.: US 10,252,991 B2
(45) Date of Patent: Apr. 9, 2019

(54) PROCESS FOR PRODUCING 7-DEHYDROCHOLESTEROL AND VITAMIN D3

(71) Applicant: KYOWA HAKKO BIO CO. LTD., Tokyo (JP)

(72) Inventors: Tetsuro Ujihara, Tokyo (JP); Satoshi Mitsuhashi, Tokyo (JP)

(73) Assignee: KYOWA HAKKO BIO CO. LTD., Tokyo (JP)

( * ) Notice: Subject to any disclaimer, the term of this patent is extended or adjusted under 35 U.S.C. 154(b) by 288 days.

(21) Appl. No.: 15/110,827

(22) PCT Filed: Jan. 14, 2015

(86) PCT No.: PCT/JP2015/050755
§ 371 (c)(1),
(2) Date: Jul. 11, 2016

(87) PCT Pub. No.: WO2015/108058
PCT Pub. Date: Jul. 23, 2015

(65) Prior Publication Data
US 2016/0332964 A1   Nov. 17, 2016

(30) Foreign Application Priority Data
Jan. 17, 2014   (JP) ................. 2014-006698

(51) Int. Cl.
C12P 33/00 (2006.01)
C07C 401/00 (2006.01)
C07J 9/00 (2006.01)

(52) U.S. Cl.
CPC ............ *C07C 401/00* (2013.01); *C07J 9/00* (2013.01); *C12P 33/00* (2013.01); C07C 2601/14 (2017.05); C07C 2602/24 (2017.05)

(58) Field of Classification Search
CPC ................................................... C12P 33/00
See application file for complete search history.

(56) References Cited

U.S. PATENT DOCUMENTS

| | | | |
|---|---|---|---|
| 6,180,805 B1 | 1/2001 | Jansen | |
| 2006/0240508 A1 | 10/2006 | Lang et al. | |
| 2009/0239837 A1 | 9/2009 | Pompon et al. | |

FOREIGN PATENT DOCUMENTS

JP   2000-26405   1/2000

OTHER PUBLICATIONS

Choe et al., "Lesions in the Sterol Δ7 reductase gene of *Arabidopsis* cause dwarfism due to a block in brassinosteroid biosynthesis", Plant J., vol. 21, No. 5 (2000) 431-43.
Fitzky et al., "7-Dehydrocholesterol-dependent proteolysis of HMG-CoA reductase suppresses sterol biosynthesis in a mouse model of Smith-Lemli-Opitz/RSH syndrome", J Clin. Invest., vol. 108, No. 6 (2001) 905-15.
Gaoua et al., "Cholesterol deficit but not accumulation of aberrant sterols is the major cause of the teratogenic activity in the Smith-Lemli-Opitz syndrome animal model", J Lipid Res., vol. 41 (2000) 637-46.
Huang et al., "Expressed sequence tag analysis of marine fungus *Schizochytrium* producing docosahexanoic acid", J. Biotechnol., vol. 138, No. 1-2 (2008) 9-16.
Steiner et al., "Sterol balance in the Smith-Lemli-Opitz syndrome: reduction in whole body cholesterol synthesis and normal bile acid production", J Lipid Res., vol. 41 (2000) 1437-47.
Veen et al., "Yeast accumulating 7-Dehydrocholesterol bears resemblance to mammalian Smith-Lemli-Opitz syndrome", Yeast Lipid Conference, Abstracts (2007).
Wang et al., "Characterization of Lipid Components in Two Microalgae for Biofuel Application", J. Am. Oil Chem. Soc., vol. 89 (2012) 135-43.
Wassif et al., "Mutations in the Human Sterol Δ7-Reductase Gene at 11q12-13 Cause Smith-Lemli-Opitz Syndrome", Am. J. Hum. Genet., vol. 63 (1998) 55-62.
Waterham et al., "Smith-Lemli-Opitz Syndrome Is Caused by Mutations in the 7-Dehydrocholesterol Reductase Gene", Am. J. Hum. Genet., vol. 63, No. 2 (1998) 329-38.
Weete et al., "Fatty Acids and Sterois of Selected Hyphochytriomycetes and Chytridiomycetes", Exp. Mycol., vol. 13 (1989) 183-95.
Weete et al., "Lipids and Ultrastructure of *Thraustochytrium* sp. ATCC 26185", Lipids, vol. 32, No. 8 (1997) 839-45.
Jira, et al., "Smith-Lemli-Opitz Syndrome and the DHCR7 Gene", Annals of Human Genetics, vol. 67, No. 3 (2003) 269-80.

*Primary Examiner* — Rebecca E Prouty
(74) *Attorney, Agent, or Firm* — Venable LLP

(57) ABSTRACT

According to the present invention, there can be provided A process for producing 7-dehydrocholesterol (hereinafter, "7DHC"), comprising culturing, in a medium, a 7DHC-producing *Labyrinthulea* microorganism in which the 7DHC reducing activity is reduced or lost as compared to a parent strain through deletion, substitution, or addition of at least one base in a gene which is present in the chromosomal DNA of the parent strain and encodes a protein having 7DHC reducing activity, and the microorganism produces 7DHC, allowing 7DHC to be produced and accumulated in the culture, and collecting the 7DHC from the culture; and a process for producing vitamin D3, comprising irradiating, with ultraviolet light, the 7DHC produced by the production process.

8 Claims, No Drawings
Specification includes a Sequence Listing.

SEQUENCE LISTING

```
<160> NUMBER OF SEQ ID NOS: 16

<210> SEQ ID NO 1
<211> LENGTH: 1437
<212> TYPE: DNA
<213> ORGANISM: Aurantiochytrium limacinum
<220> FEATURE:
<221> NAME/KEY: CDS
<222> LOCATION: (1)..(1437)

<400> SEQUENCE: 1 atg gcg ccc aaa tca aag gca gcg cct gct gtg ggg gcg tca ggc act      48
Met Ala Pro Lys Ser Lys Ala Ala Pro Ala Val Gly Ala Ser Gly Thr
1               5                   10                  15 gcc cca acc aag aag ctt agc ggc aaa tca tca tct agc aca ggc ggt      96
Ala Pro Thr Lys Lys Leu Ser Gly Lys Ser Ser Ser Ser Thr Gly Gly
                20                  25                  30 atg tgg tca ggt gag aac tcc tcg gag agt gtt ggc att ggc cct ttg     144
Met Trp Ser Gly Glu Asn Ser Ser Glu Ser Val Gly Ile Gly Pro Leu
            35                  40                  45 tgg att cgc aca gcc ttt ctc ccg gca ttt ttg gtc ctg gcc aca ccg     192
Trp Ile Arg Thr Ala Phe Leu Pro Ala Phe Leu Val Leu Ala Thr Pro
        50                  55                  60 ttg act agc atc att ctt ggt cgc gcc gtc acg tct acc gac cct aat     240
Leu Thr Ser Ile Ile Leu Gly Arg Ala Val Thr Ser Thr Asp Pro Asn
65                  70                  75                  80 gtt ggt ttt ctc agt atg ggc cag gaa gtg atc cag gag atc att gac     288
Val Gly Phe Leu Ser Met Gly Gln Glu Val Ile Gln Glu Ile Ile Asp
                85                  90                  95 acc ggt cta att gcc act tat act cgc gac gcc atg aac cct tac gtg     336
Thr Gly Leu Ile Ala Thr Tyr Thr Arg Asp Ala Met Asn Pro Tyr Val
                100                 105                 110
```

```
tgg aag atg att ggc ctt tac tgc cta gtg cag ctt ttg ctc atg cgc    384
Trp Lys Met Ile Gly Leu Tyr Cys Leu Val Gln Leu Leu Leu Met Arg
        115                 120                 125 ttc atg ccc ggt gag ata tac gag ggc cca aag agc ccc atg gga aac    432
Phe Met Pro Gly Glu Ile Tyr Glu Gly Pro Lys Ser Pro Met Gly Asn
        130                 135                 140 gtt ccc atc tat aaa gat aac gcg ttt gcc tgc tat gta gcg tcg ttt    480
Val Pro Ile Tyr Lys Asp Asn Ala Phe Ala Cys Tyr Val Ala Ser Phe
145                 150                 155                 160 gtt ctc tac ggc ctt ggc atg tac ttt ggc ctt tac aat ggt ggt gtg    528
Val Leu Tyr Gly Leu Gly Met Tyr Phe Gly Leu Tyr Asn Gly Gly Val
                165                 170                 175 gtc ttt gac cac ttt cat gag tgg gtc gcc acg atg aat att gtt gct    576
Val Phe Asp His Phe His Glu Trp Val Ala Thr Met Asn Ile Val Ala
            180                 185                 190 att atc ctc tgc tcc atc ctc tat gtc aag ggt gct gtg gct ccc tct    624
Ile Ile Leu Cys Ser Ile Leu Tyr Val Lys Gly Ala Val Ala Pro Ser
                195                 200                 205 agc act gac tct ggt ctg tct ggc aac ttt cct ttc gac tac tac tgg    672
Ser Thr Asp Ser Gly Leu Ser Gly Asn Phe Pro Phe Asp Tyr Tyr Trp
        210                 215                 220 ggc acc gag ctt tac cca cgc att ttt ggc tgg gac gtc aag gtc tat    720
Gly Thr Glu Leu Tyr Pro Arg Ile Phe Gly Trp Asp Val Lys Val Tyr
225                 230                 235                 240 acc aac tgc cgc tat ggc atg act ggc tgg gcc ttg ctt tgt gta tct    768
Thr Asn Cys Arg Tyr Gly Met Thr Gly Trp Ala Leu Leu Cys Val Ser
                245                 250                 255 ttt gct tgc gcc cag tac gag cgt ttt ggt gag att agc aac agc atg    816
Phe Ala Cys Ala Gln Tyr Glu Arg Phe Gly Glu Ile Ser Asn Ser Met
            260                 265                 270 ctc atc tct gct gtc ctt cag gtc att tac ctt gcc aag ttc cat att    864
Leu Ile Ser Ala Val Leu Gln Val Ile Tyr Leu Ala Lys Phe His Ile
                275                 280                 285 tgg gag cgt ggc tac atg ttt acc att gat atc atg cac gac cgc gct    912
Trp Glu Arg Gly Tyr Met Phe Thr Ile Asp Ile Met His Asp Arg Ala
        290                 295                 300 ggt cac tac att tgc tgg ggc tgt ctc gtc tgg gtc ccg tct gtg tac    960
Gly His Tyr Ile Cys Trp Gly Cys Leu Val Trp Val Pro Ser Val Tyr
305                 310                 315                 320 tgc tgc ccc ccc gcc ttt ctg gtg ctg cac ccg tac aac ttc cca acc   1008
Cys Cys Pro Pro Ala Phe Leu Val Leu His Pro Tyr Asn Phe Pro Thr
                325                 330                 335 tgg gta gct gtc ggc atg ttt gtt ttc tgt ctt gtg agt atc tac ctc   1056
Trp Val Ala Val Gly Met Phe Val Phe Cys Leu Val Ser Ile Tyr Leu
            340                 345                 350 aac tat gac att gat cgt cag cgc cag gag ttc cgt gcc aag gac ggc   1104
Asn Tyr Asp Ile Asp Arg Gln Arg Gln Glu Phe Arg Ala Lys Asp Gly
                355                 360                 365 aag atg aaa atc tgg ggt aag gac gcc gag tac ctc gtt gct gac tac   1152
Lys Met Lys Ile Trp Gly Lys Asp Ala Glu Tyr Leu Val Ala Asp Tyr
        370                 375                 380 cag acg ggt gat ggc aag aag cac tct tct ctt ctt ctt tac tct ggt   1200
Gln Thr Gly Asp Gly Lys Lys His Ser Ser Leu Leu Leu Tyr Ser Gly
385                 390                 395                 400 tgg tgg ggc aag gct cgc aag atc aac tac ttc ttc gag ctc tgc gct   1248
Trp Trp Gly Lys Ala Arg Lys Ile Asn Tyr Phe Phe Glu Leu Cys Ala
                405                 410                 415 ggc ttc acc tgg tct tgc att gtt gcg cac cca ttt tgt gcc ctt gca   1296
Gly Phe Thr Trp Ser Cys Ile Val Ala His Pro Phe Cys Ala Leu Ala
            420                 425                 430
```

| | | | | | | | | | | | | | | |
|---|---|---|---|---|---|---|---|---|---|---|---|---|---|---|
| tac | ccg | tat | ttc | gcc | ttc | ctt | ttc | att | ctc | ctg | att | gac | cgc | gca | tgg | 1344 |
| Tyr | Pro | Tyr | Phe | Ala | Phe | Leu | Phe | Ile | Leu | Leu | Ile | Asp | Arg | Ala | Trp |
| | 435 | | | | 440 | | | | 445 | | | | | | |

| cgc | gat | gat | gct | cgc | tgt | gcc | gac | aag | tat | ggc | gaa | aag | tgg | gag | gag | 1392 |
| Arg | Asp | Asp | Ala | Arg | Cys | Ala | Asp | Lys | Tyr | Gly | Glu | Lys | Trp | Glu | Glu |
| 450 | | | | | 455 | | | | | 460 | | | | | |

| tac | aag | aag | ctt | gtc | cct | tac | ctg | atg | att | cct | ggc | att | atc | taa | | 1437 |
| Tyr | Lys | Lys | Leu | Val | Pro | Tyr | Leu | Met | Ile | Pro | Gly | Ile | Ile |
| 465 | | | | 470 | | | | | 475 | | | | | | |

<210> SEQ ID NO 2
<211> LENGTH: 478
<212> TYPE: PRT
<213> ORGANISM: Aurantiochytrium limacinum

<400> SEQUENCE: 2

Met Ala Pro Lys Ser Lys Ala Ala Pro Ala Val Gly Ala Ser Gly Thr
1               5                   10                  15

Ala Pro Thr Lys Lys Leu Ser Gly Lys Ser Ser Ser Thr Gly Gly
            20                  25                  30

Met Trp Ser Gly Glu Asn Ser Ser Glu Ser Val Gly Ile Gly Pro Leu
            35                  40                  45

Trp Ile Arg Thr Ala Phe Leu Pro Ala Phe Leu Val Leu Ala Thr Pro
    50                  55                  60

Leu Thr Ser Ile Ile Leu Gly Arg Ala Val Thr Ser Thr Asp Pro Asn
65                  70                  75                  80

Val Gly Phe Leu Ser Met Gly Gln Glu Val Gln Glu Ile Ile Asp
                85                  90                  95

Thr Gly Leu Ile Ala Thr Tyr Thr Arg Asp Ala Met Asn Pro Tyr Val
            100                 105                 110

Trp Lys Met Ile Gly Leu Tyr Cys Leu Val Gln Leu Leu Met Arg
            115                 120                 125

Phe Met Pro Gly Glu Ile Tyr Glu Gly Pro Lys Ser Pro Met Gly Asn
    130                 135                 140

Val Pro Ile Tyr Lys Asp Asn Ala Phe Ala Cys Tyr Val Ala Ser Phe
145                 150                 155                 160

Val Leu Tyr Gly Leu Gly Met Tyr Phe Gly Leu Tyr Asn Gly Gly Val
                165                 170                 175

Val Phe Asp His Phe His Glu Trp Val Ala Thr Met Asn Ile Val Ala
            180                 185                 190

Ile Ile Leu Cys Ser Ile Leu Tyr Val Lys Gly Ala Val Ala Pro Ser
    195                 200                 205

Ser Thr Asp Ser Gly Leu Ser Gly Asn Phe Pro Phe Asp Tyr Tyr Trp
210                 215                 220

Gly Thr Glu Leu Tyr Pro Arg Ile Phe Gly Trp Asp Val Lys Val Tyr
225                 230                 235                 240

Thr Asn Cys Arg Tyr Gly Met Thr Gly Trp Ala Leu Leu Cys Val Ser
                245                 250                 255

Phe Ala Cys Ala Gln Tyr Glu Arg Phe Gly Glu Ile Ser Asn Ser Met
            260                 265                 270

Leu Ile Ser Ala Val Leu Gln Val Ile Tyr Leu Ala Lys Phe His Ile
    275                 280                 285

Trp Glu Arg Gly Tyr Met Phe Thr Ile Asp Ile Met His Asp Arg Ala
290                 295                 300

Gly His Tyr Ile Cys Trp Gly Cys Leu Val Trp Val Pro Ser Val Tyr

```
                305                 310                 315                 320
Cys Cys Pro Pro Ala Phe Leu Val Leu His Pro Tyr Asn Phe Pro Thr
                325                 330                 335
Trp Val Ala Val Gly Met Phe Val Phe Cys Leu Val Ser Ile Tyr Leu
                340                 345                 350
Asn Tyr Asp Ile Asp Arg Gln Arg Gln Glu Phe Arg Ala Lys Asp Gly
                355                 360                 365
Lys Met Lys Ile Trp Gly Lys Asp Ala Glu Tyr Leu Val Ala Asp Tyr
    370                 375                 380
Gln Thr Gly Asp Gly Lys Lys His Ser Ser Leu Leu Leu Tyr Ser Gly
385                 390                 395                 400
Trp Trp Gly Lys Ala Arg Lys Ile Asn Tyr Phe Phe Glu Leu Cys Ala
                405                 410                 415
Gly Phe Thr Trp Ser Cys Ile Val Ala His Pro Phe Cys Ala Leu Ala
                420                 425                 430
Tyr Pro Tyr Phe Ala Phe Leu Phe Ile Leu Leu Ile Asp Arg Ala Trp
                435                 440                 445
Arg Asp Asp Ala Arg Cys Ala Asp Lys Tyr Gly Glu Lys Trp Glu Glu
    450                 455                 460
Tyr Lys Lys Leu Val Pro Tyr Leu Met Ile Pro Gly Ile Ile
465                 470                 475
```

<210> SEQ ID NO 3
<211> LENGTH: 1000
<212> TYPE: DNA
<213> ORGANISM: Aurantiochytrium limacinum

<400> SEQUENCE: 3

```
gacggtcggc tgccgctggc ggcctacacg ctgaggactc cagggcctcg aattacttgc      60
ctacttgtca cctcgaaagt aggggtcaac tcttggccac ttcatgaatt cccaccattc     120
tcacatactt catgcgggtt tactgtacca tgtcttggca aggaaatgca atgcaatgca     180
gtgcaatgca atgtaatgca gtgcaatgca atgcaatgca atgcaatgcc acgctgtgcc     240
acgagaaggg tattcgcaaa gcaagaactt aatgtagata tgtgcaaggt ggattagttg     300
gatctcatca tgcaaaatgc atgcttgcaa tgcactgcgc agctatatgt aggcagtgtg     360
atgcaataca gccggccctg tgtgcttcaa gtcgctgtgt gagttgaatc ttattcgtca     420
acccaatctc tccaatgtct tatcttcttc aattcatcct cttcttccat ctattaccca     480
agaacaaaca aacaaacaaa caaacaaaca aacaaacaaa caaacaaaca aacaaaacaa     540
acaaacaaac aaacaaacaa acaaacaaac aaacaaacac aaacagagaa acacaccacg     600
acaacccaac ccaaatcaac ttgaagtctt atcgacaacg aaccctgaag ccaagaagcc     660
tcactgacga accaagcggc acggtttcca taacagagcc tttgcttgtt tgcctcttta     720
tcttttttgtt tgtctgttgt gtttgtttgt tgcttttgtt tatgataaag ttagttaggt     780
actgattagt tagttatatc gtcctgtcgc gttctgttct cagaggtata ggaggtaggg     840
tctgggacgt cagattactc agcatatcca tatcttgcga actctgcgaa ggctcgctgc     900
gccttggagg tcgtcgtgt tggcggagga tcttggagt ttggcgttgt tttgagaaag     960
agagttcctt tgaaaagtct gtgcaaaggc ttgctcgaag                          1000
```

<210> SEQ ID NO 4
<211> LENGTH: 647
<212> TYPE: DNA
<213> ORGANISM: Aurantiochytrium limacinum

<400> SEQUENCE: 4

```
attggagtga tggaatgccc tctccgtgtg gtgtatccga ttgacaaatc ttaaactcct      60
ccaagtagta ggcttcagtg cttccttgga attgagacat gaaatcatgc aacatcccac     120
cgacaggatt tatgtagtat cgcatcctct cttgttttac actctttgcc cataaattca     180
tgaacacttt cttctctttt ctctcaaaaa actagcttaa tttcatttaa gtcatgaaga     240
ctaccaatga caatcttgtc aacaaccaaa caacagctta agtttcatct aacttaagag     300
actaccatga caatcttttc acttagacaa acattatagt gaatgcattg catcataata     360
tatttattag gctttgactt caactatgtc caggcttttg ggcaccaagg accacagtta     420
caaaagcaga agatagttat gttgctatga atcaaatgaa aatgaacaaa aaagatttca     480
ggctgatatg tttcgatttg attttttgct caaatgcaat taaaagaaga cagacctcaa     540
ggtcaaatgt gattattaga atcttggaac gaatccgcac atatccagtt accaaattgt     600
tctcgcgcca ttgtgtaaat tcgctttatg atgtagcaat cacgtcc                   647
```

<210> SEQ ID NO 5
<211> LENGTH: 1005
<212> TYPE: DNA
<213> ORGANISM: Unknown
<220> FEATURE:
<223> OTHER INFORMATION: Commercially available

<400> SEQUENCE: 5

```
atgaaaagc ctgaactcac cgcgacgtct gtcgagaagt ttctgatcga aaagttcgac       60
agcgtctccg aacctgatgca gctctcggag ggcgaagaat ctcgtgcttt cagcttcgat    120
gtaggagggc gtggatatgt cctgcgggta aatagctgcg ccgatggttt ctacaaagat    180
cgttatgttt atcggcactt tgcatcggcc gcgctcccga ttccggaagt gcttgacatt    240
ggggaattca gcgagagcct gacctattgc atctcccgcc gtgcacaggg tgtcacgttg    300
caagacctgc ctgaaaccga actgcccgct gttctgcagc cggtcgcgga ggccatggat    360
gcgatcgctg cggccgatct tagccagacg agcgggttcg gcccattcgg accgcaagga    420
atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt gggccgagga ctgccccgaa gtccggcacc tcgtgcacgc ggatttcggc    600
tccaacaatg tcctgacgga caatggccgc ataacagcgg tcattgactg gagcgaggcg    660
atgttcgggg attcccaata cgaggtcgcc aacatcttct tctggaggcc gtggttggct    720
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag gtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgccccg atga                   1005
```

<210> SEQ ID NO 6
<211> LENGTH: 2490
<212> TYPE: DNA
<213> ORGANISM: Unknown
<220> FEATURE:
<223> OTHER INFORMATION: Fused gene

<400> SEQUENCE: 6

```
cgggatccaa tgcaatgtaa tgcagtgcaa tgcaatgcaa tgcaatgcaa tgccacgctg      60
tgccacgaga agggtattcg caaagcaaga acttaatgta gatatgtgca aggtggatta     120
gttggatctc atcatgcaaa atgcatgctt gcaatgcact gcgcagctat atgtaggcag     180
tgtgatgcaa tacagccggc cctgtgtgct tcaagtcgct gtgtgagttg aatcttattc     240
gtcaacccaa tctctccaat gtcttatctt cttcaattca tcctcttctt ccatctatta     300
cccaagaaca aacaaacaaa caaacaaaca aacaaacaaa caaacaaaca aacaaacaaa     360
acaaacaaac aaacaaacaa acaaacaaac aaacaaacaa acacaaacag agaaacacac     420
cacgacaacc caacccaaat caacttgaag tcttatcgac aacgaaccct gaagccaaga     480
agcctcactg acgaaccaag cggcacggtt tccataacag agcctttgct tgtttgcctc     540
tttatctttt tgtttgtctg ttgtgtttgt ttgttgcttt tgtttatgat aaagttagtt     600
aggtactgat tagttagtta tatcgtcctg tcgcgttctg ttctcagagg tataggaggt     660
agggtctggg acgtcagatt actcagcata tccatatctt gcgaactctg cgaaggctcg     720
ctgcgccttg gagggtcgtc gtgttggcgg aggatctttg gagtttggcg ttgttttgag     780
aaagagagtt cctttgaaaa gtctgtgcaa aggcttgctc gaagatgaaa aagcctgaac     840
tcaccgcgac gtctgtcgag aagtttctga tcgaaaagtt cgacagcgtc tccgacctga     900
tgcagctctc ggagggcgaa gaatctcgtg ctttcagctt cgatgtagga gggcgtggat     960
atgtcctgcg ggtaaatagc tgcgccgatg gtttctacaa agatcgttat gtttatcggc    1020
actttgcatc ggccgcgctc ccgattccgg aagtgcttga cattggggaa ttcagcgaga    1080
gcctgaccta ttgcatctcc cgccgtgcac agggtgtcac gttgcaagac ctgcctgaaa    1140
ccgaactgcc cgctgttctg cagccggtcg cggaggccat ggatgcgatc gctgcggccg    1200
atcttagcca cgacgagcgg gttcggccca tcggaccgca aggaatcggt caatacacta    1260
catggcgtga tttcatatgc gcgattgctg atccccatgt gtatcactgg caaactgtga    1320
tggacgacac cgtcagtgcg tccgtcgcgc aggctctcga tgagctgatg ctttgggccg    1380
aggactgccc cgaagtccgg cacctcgtgc acgcggattt cggctccaac aatgtcctga    1440
cggacaatgg ccgcataaca gcggtcattg actggagcga ggcgatgttc ggggattccc    1500
aatacgaggt cgccaacatc ttcttctgga ggccgtggtt ggcttgtatg gagcagcaga    1560
cgcgctactt cgagcggagg catccggagc ttgcaggatc gccgcggctc cgggcgtata    1620
tgctccgcat tggtcttgac caactctatc agagcttggt tgacggcaat ttcgatgatg    1680
cagcttgggc gcagggtcga tgcgacgcaa tcgtccgatc cggagccggg actgtcgggc    1740
gtacacaaat cgcccgcaga agcgcggccg tctggaccga tggctgtgta agtactcg     1800 ccgatagtgg aaaccgacgc cccggatgac acgtcattgg agtgatggaa tgccctctcc    1860
gtgtggtgta tccgattgac aaatcttaaa ctcctccaag tagtaggctt cagtgcttcc    1920
ttggaattga gacatgaaat catgcaacat cccaccgaca ggatttatgt agtatcgcat    1980
cctctcttgt tttacactct ttgcccataa attcatgaac actttcttct cttttctctc    2040
aaaaaactag cttaatttca tttaagtcat gaagactacc aatgacaatc ttgtcaacaa    2100
ccaaacaaca gcttaagttt catctaactt aagagactac catgacaatc ttttcactta    2160
gacaaacatt atagtgaatg cattgcatca taatatattt attaggcttt gacttcaact    2220
atgtccaggc ttttgggcac caaggaccac agttacaaaa gcagaagata gttatgttgc    2280
tatgaatcaa atgaaaatga acaaaaaaga tttcaggctg atatgtttcg atttgatttt    2340
ttgctcaaat gcaattaaaa gaagacagac ctcaaggtca aatgtgatta ttagaatctt    2400
```

```
ggaacgaatc cgcacatatc cagttaccaa attgttctcg cgccattgtg taaattcgct    2460
ttatgatgta gcaatcacgt ccggatcccg                                    2490
```

<210> SEQ ID NO 7
<211> LENGTH: 33
<212> TYPE: DNA
<213> ORGANISM: Artificial Sequence
<220> FEATURE:
<223> OTHER INFORMATION: Synthetic DNA

<400> SEQUENCE: 7

```
cgggatccaa tgcaatgtaa tgcagtgcaa tgc                                  33
```

<210> SEQ ID NO 8
<211> LENGTH: 45
<212> TYPE: DNA
<213> ORGANISM: Artificial Sequence
<220> FEATURE:
<223> OTHER INFORMATION: Synthetic DNA

<400> SEQUENCE: 8

```
gcggtgagtt caggcttttt catcttcgag caagcctttg cacag                     45
```

<210> SEQ ID NO 9
<211> LENGTH: 45
<212> TYPE: DNA
<213> ORGANISM: Artificial Sequence
<220> FEATURE:
<223> OTHER INFORMATION: Synthetic DNA

<400> SEQUENCE: 9

```
cgacgccccg gatgacacgt cattggagtg atggaatgcc ctctc                     45
```

<210> SEQ ID NO 10
<211> LENGTH: 34
<212> TYPE: DNA
<213> ORGANISM: Artificial Sequence
<220> FEATURE:
<223> OTHER INFORMATION: Synthetic DNA

<400> SEQUENCE: 10

```
cgggatccgg acgtgattgc tacatcataa agcg                                 34
```

<210> SEQ ID NO 11
<211> LENGTH: 42
<212> TYPE: DNA
<213> ORGANISM: Artificial Sequence
<220> FEATURE:
<223> OTHER INFORMATION: Synthetic DNA

<400> SEQUENCE: 11

```
gcaaaggctt gctcgaagat gaaaaagcct gaactcaccg cg                        42
```

<210> SEQ ID NO 12
<211> LENGTH: 45
<212> TYPE: DNA
<213> ORGANISM: Artificial Sequence
<220> FEATURE:
<223> OTHER INFORMATION: Synthetic DNA

<400> SEQUENCE: 12

```
atcactccaa tgacgtgtca tccggggcgt cggtttccac tatcg                     45
```

<210> SEQ ID NO 13

-continued

```
<211> LENGTH: 39
<212> TYPE: DNA
<213> ORGANISM: Artificial Sequence
<220> FEATURE:
<223> OTHER INFORMATION: Synthetic DNA

<400> SEQUENCE: 13
cggaattcgc ggccgccgtg aaggatctta gaaggagag                      39

<210> SEQ ID NO 14
<211> LENGTH: 70
<212> TYPE: DNA
<213> ORGANISM: Artificial Sequence
<220> FEATURE:
<223> OTHER INFORMATION: Synthetic DNA

<400> SEQUENCE: 14
cgggatccat aacttcgtat agcatacatt atacgaagtt atgacctgac cagtgtcaat    60
gatctcctgg                                                          70

<210> SEQ ID NO 15
<211> LENGTH: 73
<212> TYPE: DNA
<213> ORGANISM: Artificial Sequence
<220> FEATURE:
<223> OTHER INFORMATION: Synthetic DNA

<400> SEQUENCE: 15
cgggatccat aacttcgtat aatgtatgct atacgaagtt atgttttctc cttgttttgt    60
gaagtttccg ttc                                                      73

<210> SEQ ID NO 16
<211> LENGTH: 45
<212> TYPE: DNA
<213> ORGANISM: Artificial Sequence
<220> FEATURE:
<223> OTHER INFORMATION: Synthetic DNA

<400> SEQUENCE: 16
atatgccctg caggcggccg cccaaaacag aagccatagg tgatg                    45
```

PROCESS FOR PRODUCING 7-DEHYDROCHOLESTEROL AND VITAMIN D3

This application is a national phase of PCT Application No. PCT/JP2015/050755 filed on Jan. 14, 2015, which in turn claims benefit of Japanese Application No. 2014-006698filed Jan. 17, 2014.

TECHNICAL FIELD

The present invention relates to a process for producing 7-dehydrocholesterol (hereinafter, also referred to as "7DHC") using *Labyrinthulea* microorganisms, and to a process for producing vitamin D3 comprising irradiating, with ultraviolet light, the 7DHC produced by the production process.

BACKGROUND ART

Vitamin D3 is a vitamin involved in various functions including metabolism and homeostasis maintenance of calcium and phosphorus, and bone formation, and is produced from cholesterol in the human body. However, because the quantity of vitamin D3 produced in the body is smaller than the required quantities, vitamin D3 needs to be ingested through food, drug products, or supplements.

Vitamin D3 contained in drug products and supplements is produced mainly through ultraviolet irradiation of 7DHC produced by chemical transformation from cholesterol obtained from wool. However, use of animal-derived materials as source materials of drug products and supplements tends to be avoided due to the concerns of BSE and zoonosis, and there is a need for vitamin D3 derived from non-animal. Vitamin D3 derived from non-animals can be produced through ultraviolet irradiation of 7DHC derived from non-animal.

Generally, sterols produced by microorganisms are ergosterols. However, some members of oomycetes and *Labyrinthulea* microorganisms are known to produce cholesterol (Non-Patent Documents 1 to 3). 7DHC is converted into cholesterol by the action of 7DHC reductase. Therefore, it is theoretically possible to produce non-animal-derived 7DHC by reducing or eliminating the 7DHC reducing activity in these microorganisms and using the same for fermentative production or the like.

However, there are reports that significant amount of 7DHC is not accumulated in humans, mice, and budding yeasts. Specifically, there are reports that in humans and mice, 7DHC production involving a loss of 7DHC reducing activity causes decomposition of HMG-CoA reductase that catalyzes the rate-limiting step of cholesterol synthesis, and significantly reduces 7DHC accumulation (Non-Patent Documents 4 to 6). As to the budding yeasts, there is a report that 7DHC production involving introduction of 7DHC reductase significantly reduces 7DHC accumulation (Non-Patent Document 7).

Further, there are reports that a loss of 7DHC reducing activity causes Smith-Lemli-Opitz syndrome in humans (Non-Patent Document 8), and expression of a dwarf phenotype in plants (Non-Patent Document 9). That is, a reduction or a loss of 7DHC reducing activity was believed to have adverse effect on the growth of the host organism.

RELATED ART

Non-Patent Document

Non-Patent Document 1: Exp. Mycol. (1989) 13:183-195
Non-Patent Document 2: Lipids (1997) 32:839-845
Non-Patent Document 3: J. Am. Oil Chem. Soc. (2012) 89:135-143
Non-Patent Document 4: J Clin. Invest. (2001) 108:905-915
Non-Patent Document 5: J Lipid Res. (2000) 41:1437-1447
Non-Patent Document 6: J Lipid Res. (2000) 41:637-646
Non-Patent Document 7: Yeast Lipid Conference, Abstracts (2007), Internet<URL: http://aperto.unito.it/handle/2318/209#.Uq5WatJdW4E>
Non-Patent Document 8: Am. J. Hum. Genet. (1998) 63:55-62
Non-Patent Document 9: Plant J. (2000) 21:431-443

DISCLOSURE OF INVENTION

Problems to be Solved by the Invention

It is an object of the present invention to provide a process for efficiently producing 7DHC using a *Labyrinthulea* microorganism, and a process for producing vitamin D3 comprising irradiating, with ultraviolet light, 7DHC produced by the production process.

Means for Solving the Problems

The present invention relates to the following (1) to (4).
(1) A process for producing 7-dehydrocholesterol (hereinafter, "7DHC"), comprising:
  culturing, in a medium, a 7DHC-producing *Labyrinthulea* microorganism in which the 7DHC reducing activity is reduced or lost as compared to a parent strain through deletion, substitution, or addition of at least one base in a gene which is present in the chromosomal DNA of the parent strain and encodes a protein having 7DHC reducing activity, and the microorganism produces 7DHC;
  allowing 7DHC to be produced and accumulated in the culture; and
  collecting the 7DHC from the culture.
(2) The production process described in (1) above, wherein the gene encoding a protein having 7DHC reducing activity is a gene having any of the following DNAs [1] to [6]:
  [1] a DNA encoding a protein having the amino acid sequence represented by SEQ ID NO: 2;
  [2] a DNA encoding a mutated protein consisting of the amino acid sequence represented by SEQ ID NO: 2 with deletion, substitution, or addition of 1 to 20 amino acids, and having 7DHC reducing activity;
  [3] a DNA encoding a homologous protein having at least 95% identity with the amino acid sequence represented by SEQ ID NO: 2, and having 7DHC reducing activity;
  [4] a DNA having the base sequence represented by SEQ ID NO: 1;
  [5] a DNA that hybridizes with DNA consisting of a base sequence complementary to the base sequence represented by SEQ ID NO: 1 under stringent conditions, and encodes a homologous protein having 7DHC reducing activity; and
  [6] a DNA having at least 95% identity with the base sequence represented by SEQ ID NO: 1, and encoding a homologous protein having 7DHC reducing activity.
(3) The production process described in (1) above, wherein the *Labyrinthulea* microorganism is a *Labyrinthulea* microorganism of the genus *Schizochytorium*, *Thraustochytrium*, *Aurantiochytrium*, *Parietichytrium*, *Laby-* rinthula, Althomia, Aplanochytrium, Japonochytrium, Labyrinthuloides, Ulkenia, Oblongichytrium, Botryochytrium, or Sicyoidochytrium.

(4) A process for producing vitamin D3, comprising irradiating the 7DHC produced by the production process described in any one of (1) to (3) above with ultraviolet light.

Effects of the Invention

According to the present invention, a process for efficiently producing 7DHC using a Labyrinthulea microorganism, and a process for producing vitamin D3 comprising irradiating, with ultraviolet light, 7DHC produced by the production process can be provided.

EMBODIMENTS FOR CARRYING OUT THE INVENTION

1. Labyrinthulea Microorganism Used in Production Process of the Present Invention The Labyrinthulea microorganism used in the production process of the present invention is a 7DHC-producing Labyrinthulea in which the 7DHC reducing activity is reduced or lost as compared to a parent strain through deletion, substitution, or addition of at least one base in a gene which is present in the chromosomal DNA of the parent strain and encodes a protein having 7DHC reducing activity, and the microorganism produces 7DHC.

Here, "parent strain" means an original strain subjected to gene modification, transformation, and the like. An original strain subjected to transformation by gene introduction is also called "host strain."

The parent strain is not particularly limited, as long as it is a Labyrinthulea microorganism capable of producing cholesterol to such an extent that it can be collected from cells or medium after culture in a medium. Preferred examples include Labyrinthulea microorganisms of the genus Schizochytrium, Thraustochytrium, Aurantiochytrium, Parietichytrium, Labyrinthula, Althomia, Aplanochytrium, Japonochytrium, Labyrinthuloides, Ulkenia, Oblongichytrium, Botryochytrium, or Sicyoidochytrium. More preferred examples include Labyrinthulea microorganisms of the genus Schizochytorium, Thraustochytrium, Aurantiochytrium, or Parietichytrium. Further preferred examples include Aurantiochytrium limacinum ATCC MYA-1381, Thraustochytrium aureum ATCC34304, Thraustochytrium sp. ATCC26185, Schizochytrium sp. AL1Ac, Schizochytrium aggregatum ATCC28209, Ulkenia sp. ATCC 28207, Schizochytrium sp. SEK210 (NBRC 102615), Schizochytrium sp. SEK345 (NBRC 102616), Botryochytrium radiatum SEK353 (NBRC 104107), and Parietichytrium sarkarianum SEK364 (FERM ABP-11298). Most preferred examples include Aurantiochytrium limacinum ATCC MYA-1381.

7DHC reducing activity is the activity that reduces the double bond at position 7 of 7DHC to produce cholesterol.

In the present invention, the "protein having 7DHC reducing activity" is not limited, as long as it is a protein encoded by a gene on a genomic chromosome of a Labyrinthulea microorganism, and that has 7DHC reducing activity, but is preferably any of the following proteins [1] to [3]:

[1] a protein having the amino acid sequence represented by SEQ ID NO: 2;

[2] a mutated protein consisting of the amino acid sequence represented by SEQ ID NO: 2 with the deletion, substitution, or addition of 1 to 20, preferably 1 to 10, most preferably 1 to 5 amino acids, and having 7DHC reducing activity; and

[3] a homologous protein having at least 95%, preferably at least 97%, more preferably at least 98%, most preferably at least 99% identity with the amino acid sequence represented by SEQ ID NO: 2, and having 7DHC reducing activity.

The "homologous protein" refers to a protein which is possessed by organisms found in nature, and is encoded by a gene that is believed to share the same evolutional origin with a gene encoding an original protein because the homologous protein has a structure and functions similar to those of the original protein.

The identify of the amino acid sequences and base sequences can be determined using the algorithm BLAST [Pro. NATdomainl. Acad. Sci. USA, 90, 5873(1993)] by Karlin and Altschul, and FASTA [Methods Enzymol., 183, 63 (1990)]. Programs called BLASTN and BLASTX based on the algorithm BLAST have been developed [J. Mol. Biol., 215, 403(1990)]. For analysis of base sequences using BLASTN based on BLAST, the parameters are, for example, Score=100, and word length=12. For analysis of amino acid sequences using BLASTX based on BLAST, the parameters, for example, score=50, and word length=3. When using BLAST and Gapped BLAST programs, the programs are used with their default parameters. Specific techniques for these analysis methods are known.

The "mutated protein" means a protein obtained after artificially deleting or substituting an amino acid residue in the original protein, or adding an amino acid residue to the protein.

In the above-mentioned mutated protein, "deletion", "substitution", "insertion", or "addition" of an amino acid may mean "deletion", "substitution", or "addition" of 1 to 20, preferably 1 to 10, most preferably 1 to 5 amino acids at any positions in the same sequence.

The amino acid deleted, substituted, or added may be a naturally occurring amino acid or a non-naturally occurring amino acid. Examples of naturally occurring amino acids include L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, and L-cysteine.

Examples of mutually substitutable amino acids are listed below. The amino acids of the same group can be mutually substituted for one another.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine The "gene encoding a protein having 7DHC reducing activity" is not limited, as long as it is a gene present on a genomic chromosome of a Labyrinthulea microorganism, and encodes a protein having 7DHC reducing activity, but is preferably a gene having any of the following DNAs [4] to [7]:

[4] a DNA encoding any of the proteins [1] to [3] above;

[5] a DNA having the base sequence represented by SEQ ID NO: 1;

[6] a DNA that hybridizes with DNA consisting of a base sequence complementary to the base sequence represented by SEQ ID NO: 1 under stringent conditions, and encodes a homologous protein having 7DHC reducing activity; and

[7] a DNA having at least 95%, preferably at least 97%, more preferably at least 98%, most preferably at least 99% identity with the base sequence represented by SEQ ID NO: 1, and encoding a homologous protein having 7DHC reducing activity.

The "gene" refers to DNA which may comprise, in addition to a protein coding region, a transcriptional regulatory region, a promoter region, a terminator region, and the like.

The term "hybridize" means that a DNA having a specific base sequence, or a part of the DNA forms a conjugate with other DNA in a complementary fashion. Accordingly, a DNA of a specific base sequence, or a partial base sequence of the DNA may be a DNA that is useful as a probe for northern blot or southern blot analysis, or a DNA of a length that can be used as an oligonucleotide primer for PCR analysis. Examples of the DNA used as a probe include the DNA of at least 100 bases, preferably at least 200 bases, more preferably at least 500 bases. Examples of the DNA used as a primer includes the DNA of at least 10 bases, preferably at least 15 bases.

DNA hybridization experimental techniques are well known. For example, experiments may be conducted after setting hybridization conditions according standard textbooks, including Molecular Cloning, Second Edition, Third Edition (2001), Methods for GenERdomainal and Molecular BactEriology, ASM Press (1994), and Immunology methods manual, Academic press (Molecular).

Further, also according to an instructional manual accompanying a commercially available hybridization kit, a DNA which hybridizes under stringent conditions can be obtained. The commercially available hybridization kit may include, for example, Random Primed DNA Labeling Kit (manufactured by Roche Diagnostics GmbH), with which a probe is produced by a random prime method, and hybridization is performed under stringent conditions, and the like.

The above-described stringent conditions may include conditions in which a filter on which a DNA has been immobilized and a probe DNA are incubated overnight at 42° C. in a solution containing 50% formamide, 5×SSC (750 mM sodium chloride and 75 mM sodium citrate), 50 mM sodium phosphate (pH 7.6), 5×Denhardt's solution, 10% dextran sulfate, and 20 μg/l of a denatured salmon sperm DNA, and then the filter is washed in, for example, a 0.2×SSC solution at about 65° C.

The above-described various conditions can also be set by adding or changing a blocking reagent to be used for suppressing the background in the hybridization experiment. The addition of the blocking reagent may be accompanied by a change in hybridization conditions for adapting the conditions.

The DNA which can hybridize under the above-described stringent conditions may include a DNA consisting of a nucleotide sequence having at least 95% or more, preferably 97% or more, more preferably 98% or more, and most preferably 99% or more identity to the base sequence represented by SEQ ID NO:1 when performing calculation based on the above-described parameters using, for example, the program such as BLAST or FASTA described above.

With respect to the introduction of deletion, substitution, or addition of at least one base into the gene that encodes a protein having 7DHC reducing activity, the number and the type of base are not limited, as long as the deletion, substitution, or addition of at least one base makes the 7DHC reducing activity weaker than in the parent strain, or eliminates the 7DHC reducing activity. However, examples thereof include in the promoter and the transcriptional regulatory region, the deletion of at least one base, preferably at least 10 bases, more preferably at least 20 bases, further preferably the entire region; in the coding region, deletion of at least one base, preferably at least 10 bases, more preferably at least 20 bases, further preferably at least 100 bases, particularly preferably at least 200 bases, most preferably the entire region of the coding region.

The substitution of one or more bases may be a substitution that introduces a nonsense codon through substitution of at least one base within 150 bases, preferably 100 bases, more preferably 50 bases, particularly preferably 30 bases, most preferably 20 bases from the 5' end of the coding region.

The addition of at least one base may be an addition of a DNA fragment of at least one base, preferably at least 50 bases, more preferably at least 100 bases, further preferably at least 200 bases, particularly preferably at least 500 bases, most preferably at least 1 kb immediately after a base within 150 bases, preferably 100 bases, more preferably 50 bases, particularly preferably 30 bases, most preferably 20 bases from the 5' end of the coding region. Most preferably, the addition of one or more bases is an insertion of a gene such as a hygromycin resistant gene.

A reduction of 7DHC reducing activity as compared to the parent strain can be confirmed by, for example, quantifying the amount of the transcript of the DNA of any of [4] to [7] above by northern analysis or RT-PCR, and comparing the result with the parent strain, or quantifying the yield of the protein of any of [1] to [3] above by SDS-PAGE or an assay using an antibody, and comparing the result with the parent strain.

A reduction in the specific activity of the protein of any of [1] to [3] above as compared to the parent strain also may be taken as confirmation. A reduction in the specific activity of the protein relative to the parent strain can be confirmed by culturing the *Labyrinthulea* microorganism using the method in Section 3 below, and comparing the accumulated 7DHC in the culture with that of the parent strain.

Being capable of producing 7DHC means the possession of capability to produce 7DHC to such an extent that the 7DHC can be collected from the cells or medium of a cultured *Labyrinthulea* microorganism in which 7DHC reducing activity is reduced or lost as compared to the parent strain through deletion, substitution, or addition of at least one bases in a gene which is present in chromosomal DNA of the parent strain and encodes a protein having 7DHC reducing activity.

2. Method of Production of Labyrinthulea Microorganism Used in Production Process of the Present Invention The *Labyrinthulea* microorganism used in the production process of the present invention may be produced by reducing or eliminating the 7DHC reducing activity as compared to the parent strain through deletion, substitution, or addition of at least one base in a gene which is present in chromosomal DNA of the parent strain and has the DNA of any of [4] to [7].

The method for introducing the deletion, substitution, or addition of at least one base into a gene which is present in chromosomal DNA of the parent strain is not limited, and ordinary methods such as common mutagenesis, gene substitution methods using recombinant DNA techniques, and the like may be used, as long as a mutation can be introduced into chromosomal DNA of the *Labyrinthulea* microorganism.

The parent strain may be a wild-type strain, provided that it is a *Labyrinthulea* microorganism capable of producing cholesterol, and having 7DHC reducing activity. When the wild-type strain lacks the cholesterol producing capability, the parent strain may be a breeding strain that has been artificially endowed with the cholesterol producing capability.

The *Labyrinthulea* microorganism may be artificially endowed with the cholesterol producing capability by using, for example, the following methods:

(a) a method that weakens or cancels at least one of the mechanisms controlling the cholesterol biosynthesis;

(b) a method that enhances the expression of at least one of the enzymes involved in the cholesterol biosynthesis;

(c) a method that increases the copy number of at least one of the enzyme genes involved in the cholesterol biosynthesis;

(d) a method that attenuates or blocks at least one of the metabolic pathways that branch out of the cholesterol biosynthesis pathway into producing metabolites other than the target substance; and (e) a method that selects a cell line having higher resistance to cholesterol analogs as compared to the wild-type strain.

These known methods may be used alone or in combination.

The parent strain that can be used to prepare the *Labyrinthulea* microorganism having a cholesterol producing capability may be any strain, as long as it is a *Labyrinthulea* microorganism to which the foregoing methods (a) to (e) are applicable. Preferred examples include *Labyrinthulea* microorganisms of the genus *Schizochytrium, Thraustochytrium, Aurantiochytrium, Parietichytrium, Labyrinthula, Althornia, Aplanochytrium, Japonochytrium, Labyrinthuloides, Ulkenia, Oblongichytrium, Botryochytrium,* and *Sicyoidochytrium*. More preferred examples include *Labyrinthulea* microorganisms of the genus *Schizochytorium, Thraustochytrium, Aurantiochytrium,* and *Parietichytrium*. Further preferred examples include *Aurantiochytrium limacinum* ATCC MYA-1381, *Thraustochytrium aureum* ATCC34304, *Thraustochytrium* sp. ATCC26185, *Schizochytrium* sp. AL1Ac, *Schizochytrium aggregatum* ATCC28209, *Ulkenia* sp. ATCC 28207, *Schizochytrium* sp. SEK210 (NBRC 102615), *Schizochytrium* sp. SEK345 (NBRC 102616), *Botryochytrium radiatum* SEK353 (NBRC 104107), and *Parietichytrium sarkarianum* SEK364 (FERM ABP-11298). Most preferred examples include *Aurantiochytrium limacinum* ATCC MYA-1381.

Mutagenesis may be achieved, for example, by a method that uses N-methyl-N'-nitro-N-nitrosoguanidine (NTG) (Microorganism Experiment Manual, 1986, p. 131, Kodansha Scientific), by ultraviolet irradiation, or the like.

As an example of gene substitution methods using recombinant DNA techniques, a recombinant DNA is created by introducing substitution, deletion, or addition of at least one base to a gene in vitro, and the recombinant DNA is introduced into the parent strain to substitute the gene originally present on the chromosome through, for example, homologous recombination or the like.

The DNAs of [4] to [7] above may be obtained by, for example, PCR using an oligoDNA designed and synthesized from the base sequence represented by SEQ ID NO: 1, and using a template chromosomal DNA prepared from a *Labyrinthulea* microorganism, according to the method of Saito et al. [BIOCHIMICA ET BIOPHYSICA ACTA (1963) 72:619-629].

Examples of the specific DNA that can be obtained include DNA having the base sequence represented by SEQ ID NO: 1.

The DNA may also be obtained by using a hybridization method that uses a part of or all of the DNA as a probe, a method that chemically synthesizes DNA having the base sequence using known techniques, or the like.

The DNA of [4] above that encodes the homologous protein of [3] above, and the DNAs that encodes the homologous proteins of [6] and [7] may be obtained by, for example, searching various gene sequence databases for a base sequence having at least 95%, preferably at least 97%, further preferably at least 98%, most preferably at least 99% identity with the base sequence represented by SEQ ID NO: 1, or searching various protein sequence databases for an amino acid sequence having at least 95%, preferably at least 97%, further preferably at least 98%, most preferably at least 99% identity with the amino acid sequence represented by SEQ ID NO: 2, and performing the same methods used to obtain the DNAs above, using a probe DNA or a primer DNA that can be designed from the base sequence or the amino acid sequence obtained after the search, and a microorganism having the DNA.

The base sequence of DNA may be determined through analysis with a base sequence analyzer, such as a 373A DNA Sequencer (manufactured by PerkinElmer Co., Ltd.), using an ordinary base-sequence analysis method, for example, such as the dideoxy method [PROCEEDINGS OF THE NATIONAL ACADEMY OF SCIENCES (1977) 74(12): 5463-5467].

When the DNA obtained is found to be a partial-length DNA after the determination of its base sequence, a full-length DNA may be obtained by using techniques such as southern hybridization with a chromosomal DNA library, using the partial-length DNA as a probe.

Such techniques are described in, for example, Molecular Cloning: A Laboratory Manual, 3rd ed., Cold Spring Harbor Laboratory Press (2001) [Hereinafter, simply "Molecular Cloning, 3rd Ed."], Current Protocols in Molecular Biology, John Wiley & Sons (1987-1997) (hereinafter, simply "Current Protocols in Molecular Biology"), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985), J. Bacteriol., 182, 6884 (2000), Gene 77: 61-68, 1989, and the like.

Any method may be used for the introduction of the recombinant DNA into the parent strain, provided that the DNA can be introduced into a *Labyrinthulea* microorganism. Examples of such methods include electroporation [Appl. Microbiol. Biotech., 52, 541 (1999)], and the protoplast method [J. Bacteriol., 159, 306 (1984)].

While gene substitution on a chromosome of the parent strain can be achieved with methods such as above, the method is not limited to these, and other gene substitution methods are also usable, provided that a gene on a chromosome of a *Labyrinthulea* microorganism can be substituted.

By introducing deletion, substitution, or addition of at least one base in a gene on a chromosome of the parent strain, the activity of the protein encoded by the gene can be reduced or eliminated with good probability [An Introduction to Genetic Analysis. 7th edition (2000), Griffiths A J F, Miller J H, Suzuki D T et al., New York: W. H. Freeman].

Production and accumulation of 7DHC in a cultured medium of a *Labyrinthulea* microorganism created by using the foregoing methods can be confirmed by homogenizing the *Labyrinthulea* microorganism with, for example, a ultrasonic or a Dyno-Mill after separating the cells from the culture, and detecting the 7DHC present in the extract by gas chromatography after solvent extraction with, for example, chloroform, hexane, butanol, or the like.

3. 7DHC Production Process of the Present Invention

A 7DHC production process of the present invention is a process for producing 7DHC which comprises culturing the *Labyrinthulea* microorganism created by using the methods in Section 2 above in a medium, and allow 7DHC to be produced and accumulated in the medium, and collecting the 7DHC from the culture.

The *Labyrinthulea* microorganism may be cultured by inoculating it in a suitable medium, and culturing the cells according to an ordinary method.

The medium may be any known medium. Examples of carbon sources include, in addition to carbohydrates such as glucose, fructose, and galactose, oils and fats such as oleic acid, and soybean oil, and glycerol and sodium acetate. The carbon source may be used in a concentration of, for example, 20 to 300 g per liter of medium. In a particularly preferred embodiment, the carbon source may be fed to continue culture after all the carbon sources originally contained in the medium were consumed. By performing culture under these conditions, more carbon source can be consumed, and the yield of 7DHC can increase.

Examples of nitrogen sources include organic nitrogen such as yeast extracts, corn steep liquors, polypeptone, sodium glutamate, and urea, and inorganic nitrogen such as ammonium acetate, ammonium sulfate, ammonium chloride, sodium nitrate, ammonium nitrate, and ammonia.

Mineral salts, such as potassium phosphate, may be used in appropriate combinations.

Preferably, after the medium is prepared, pH thereof is adjusted to the range of 4.0 to 9.5 by adding a suitable acid or base, and then the medium is sterilized with an autoclave.

Preferably, the culture temperature of the *Labyrinthulea* microorganism is controlled to a temperature that allows for 7DHC production. Typically, the culture temperature is 10 to 45° C., preferably 20 to 37° C.

During culturing, pH is typically 3.5 to 9.5, preferably 4.5 to 9.5, most preferably 5.0 to 8.0.

Culture period may be, for example, 2 to 7 days, and the culturing may be performed under aerated stirred conditions.

The *Labyrinthulea* microorganism that has accumulated a high concentration of 7DHC during culture can be obtained in high concentration, typically about 20 to 100 g in terms of a dry cell weight per liter of the medium. Separation of the culture medium and the *Labyrinthulea* microorganism from the culture may be performed by using an ordinary method known to a skilled person, for example, such as centrifugation, and filtration.

The *Labyrinthulea* microorganism separated from culture is homogenized with, for example, an ultrasonic or a Dyno-Mill, and 7DHC can be obtained after solvent extraction with, for example, chloroform, hexane, or butanol. The method for extracting 7DHC and other sterols from the cells of microorganisms is described in L. Parks et al. [Methods in Enzymology 111 Edited (1985) by L Rifling, L. Parks, C. Bottema, R. Rodriguez and Thomas Lewis, p. 333-339].

The crude 7DHC thus obtained may be further purified by using a method known to a skilled person, in particular, the method described in Boselli E, Velazco V, CaboniMf and Lercker G J, ChromatogrA. 2001 May 11; 917 (1-2): 239-44.

It is also possible to use other methods, such as methods used to extract cholesterol from wool. In particular, a skilled person may refer to the methods described in U.S. Pat. No. 2,688,623, or U.S. Pat. No. 2,650,929, or British Patent No. GB690879, GB646227, or GB613778.

In a preferred embodiment of the present invention, 7DHC is present in *Labyrinthulea* cells in a proportion of more than 20%, preferably more than 35% of the total sterol produced by the *Labyrinthulea* microorganism created by using the method described in Section 2 above.

4. Vitamin D3 Production Process of the Present Invention

A vitamin D3 production process of the present invention is a process for producing vitamin D3 which comprises irradiating the 7DHC produced by the production process of Section 3 above with ultraviolet light.

Vitamin D3 can be produced by irradiating the 7DHC obtained by using the production process of Section 3 above with ultraviolet light, such as with a mercury lamp, followed by heating. The heating temperature is preferably 50 to 100° C., most preferably 80° C. to 100° C. The heating time is preferably 5 to 300 minutes, more preferably 10 to 100 minutes.

The obtained vitamin D3 may be concentrated by using techniques such as high-performance liquid chromatography, and supercritical chromatography, and collected to obtain highly concentrated purified vitamin D3.

REFERENCE EXAMPLE

A Search for *Labyrinthulea* Microorganism that Accumulates Significant Amount of Cholesterol 7DHC has a structure in which a double bond is introduced at carbon 7 of cholesterol. In order to create a *Labyrinthulea* microorganism that produces significant amounts of 7DHC through metabolic modification, it is accordingly desirable that the parent strain is a *Labyrinthulea* microorganism that accumulates significant amount of cholesterol.

To this end, the present inventors examined the cholesterol productivity of *Labyrinthulea* microorganisms deposited at official institutions, as follows.

*Aurantiochytrium* sp. NBRC103268, *Aurantiochytrium* sp. NBRC103269, *Parietichytrium sarkarianum* NBRC104108, *Schizochytrium* sp. ATCC20888, and *Aurantiochytrium limacinum* ATCC MYA-1381 were cultured in evaluation liquid medium (9% glucose, 1% yeast extract, 1% peptone, 50% artificial sea water) at 30° C. for 72 hours.

Lipids were extracted from each culture according to the method of Bligh & Dyer [Bligh E G and Dyer W J, Can. J. Biochem. Physiol. 37 911 (1959)], and dried under reduced pressure. The dry lipids were dissolved in 0.1N KOH-methanol, and processed at 60° C. for 30 minutes to saponify. For extraction of the free sterols obtained after the saponification process, an equal amount of water was added, and the solution was extracted three times with hexane used in two times the volume of water. The extracted hexane fraction was concentrated under reduced pressure, and analyzed by gas chromatography. For quantification, 5α Cholestane (manufactured by Sigma) was added at an early stage of extraction, and used as internal standard. For cholesterol identification, cholesterol (manufactured by Tokyo Chemical Industry) was used as external standard.

The results are presented in Table 1. As can be seen in Table 1, *Aurantiochytrium limacunum* ATCC MYA-1381 was found to have a high cholesterol producing capability.

[Gas Chromatography Conditions]

Column: HR-52 (Shinwa Chemical Industries Ltd.) 0.25 mm×30 cm, 0.25 mm

Carrier gas: $N_2$, 31 ml/min

Column temperature: 280° C.

Detection: FID

TABLE 1

Cholesterol Production by Labyrinthulea Microorganisms

| Labyrinthulea microorganism | Growth (OD 660) | Cholesterol (mg/L) |
|---|---|---|
| NBRC103268 | 14 ± 3.2 | 58 ± 18 |
| NBRC103269 | 30 ± 7.4 | 161 ± 19 |
| NBRC104108 | 3.6 ± 0.2 | 7.6 ± 3.5 |
| ATCC MYA-1381 | 35 ± 5.7 | 205 ± 37 |
| ATCC 20888 | 21 ± 4.9 | 151 ± 4.2 |

Examples of the present invention are shown below, but the present invention is not limited by the following Examples.

Example 1

Creation of *Labyrinthulea* Microorganism in which 7DHC Reducing Activity is Lost The 7DHC reducing activity was eliminated in the *Aurantiochytrium limacunum* ATCC MYA-1381 (hereinafter, "MYA-1381") that was found to accumulate significant amount of cholesterol in Reference Example, as follows.

Genomic DNA of MYA-1381 was prepared by using an ordinary method. DNA fragments were amplified by PCR, using DNAs consisting of the base sequences denoted as "primer set" in Table 2 as primer sets, and the genomic DNA as a template.

TABLE 2

| Primer set (SEQ ID NO:) | Amplified DNA fragment |
|---|---|
| 7 and 8 | Pyruvate kinase promoter (SEQ ID NO: 3) |
| 9 and 10 | Actin terminator (SEQ ID NO: 4) |

Further, hygromycin resistant gene (SEQ ID NO: 5) was amplified by PCR, using DNAs of the base sequences represented by SEQ ID NOS: 11 and 12 as a primer set, and a drug-resistant gene expression cassette (manufactured by Genebridges) as a template.

By using a mixture of these three amplified DNA fragments as a template, PCR was run using DNAs of the base sequences represented by SEQ ID NOS: 7 and 10 as a primer set. Because SEQ ID NOS: 8 and 11, and SEQ ID NOS: 9 and 12 have complementary sequences at the 5' ends, the three DNA fragments can bind in the PCR. That is, the PCR was performed to prepare an expression cassette fragment of a hygromycin resistant gene having an MYA-1381-derived pyruvate kinase promoter and actin terminator (SEQ ID NO: 6).

Each DNA fragment was amplified by PCR, using DNAs of the base sequences denoted as "primer set" in Table 3 as primer sets, and genomic DNA of MYA-1381 as a template. The restriction enzyme sequence described in "Restriction Enzyme Sequence" of Table 3 was added to each DNA fragment.

TABLE 3

| Primer set (SEQ ID NO:) | Amplified DNA fragment | Restriction enzyme sequence |
|---|---|---|
| 13 and 14 | Upstream region of DNA consisting of base sequence represented by SEQ ID NO: 1 | EcoRI and BamHI |
| 15 and 16 | Downstream region of DNA consisting of base sequence represented by SEQ ID NO: 1 | Sse8387I and BamHI |

The amplified fragment in the upstream region was treated with EcoRI and BamHI, and the amplified fragment in the downstream region was treated with Sse8387I and BamHI, and these were ligated to EcoRI- and Sse8387I-treated pUC18 [J. Methods in Enzymology (1983) 101:20-78] to obtain a plasmid.

The plasmid was treated with BamHI, and ligated to the hygromycin resistant gene expression cassette fragment obtained above (SEQ ID NO: 6) which was treated with BamHI. This produced a plasmid in which the hygromycin resistant gene expression cassette was introduced to the upstream and downstream regions of the DNA of the base sequence represented by SEQ ID NO: 1. The plasmid was named pUCDHCR-hyg.

The pUCDHCR-hyg was treated with NotI to obtain a DNA fragment that had the hygromycin resistant gene expression cassette inserted to the upstream and downstream regions of the DNA consisting of the base sequence represented by SEQ ID NO: 1.

The DNA fragment was introduced into MYA-1381 by electroporation to obtain a hygromycin resistant strain. This strain was named MYA-1381Δ7DHCR. It was confirmed by PCR that MYA-1381Δ7DHCR had a substitution of the DNA consisting of the base sequence represented with SEQ ID NO: 1 with the DNA fragment having the hygromycin resistant gene expression cassette inserted to the upstream and downstream regions of the DNA consisting of the base sequence represented by SEQ ID NO: 1.

Further, as discussed below in Example 2, since the MYA-1381Δ7DHCR strain did not produce the cholesterol produced by the parent strain, but produced 7DHC instead, it was concluded that the MYA-1381Δ7DHCR had lost the 7DHC reducing activity.

Example 2

Production of 7DHC

The MYA-1381 (parent strain) and MYA-1381Δ7DHCR strains were cultured in the same manner as in Reference Example, using a liquid medium (12% glucose, 1% yeast extract, 1% peptone, 50% artificial sea water). After the culturing, the cells were collected, and a gas chromatography analysis was performed as in Reference Example. The results are shown in Tables 4 and 5.

The MYA-1381Δ7DHCR did not produce the cholesterol that is produced in the parent strain, but produced 7DHC instead.

TABLE 4

| Labyrinthulea microorganism | Growth (OD 660 nm) | Cholesterol (mg/L) |
|---|---|---|
| MYA-1381 | 54 ± 9.3 | 435 ± 41 |

TABLE 5

| Labyrinthulea microorganism | Growth (OD 660 nm) | 7DHC (mg/L) |
|---|---|---|
| MYA-1381Δ7DHCR | 66 ± 6.8 | 325 ± 37 |

The results were far more desirable than the previously reported results for budding yeasts. This is believed to be due to the use of the cholesterol producing *Labyrinthulea* microorganism as the parent strain.

It was thought from the previous findings (Non-Patent Documents 4 to 9) that reducing or eliminating the 7DHC reducing activity in a *Labyrinthulea* microorganism would have a detrimental effect on growth, and largely reduce an amount of accumulated 7DHC. However, the MYA-1381Δ7DHCR strain had the same level of growth as the parent strain, and accumulated significant amount of 7DHC.

Example 3

Production of Vitamin D3

The 7DHC manufactured in Example 2 was irradiated with 300-nm UV light, and processed at 100° C. for 30 minutes. The product was then analyzed by gas chromatography in the manner described in Reference Example.

As a result, it was confirmed that 7DHC was converted into vitamin D3.

INDUSTRIAL APPLICABILITY

According to the present invention, a process for efficiently producing 7DHC using a *Labyrinthulea* microorganism, and a process for producing vitamin D3 comprising irradiating, with ultraviolet light, 7DHC produced by the production process can be provided.

SEQUENCE LISTING FREE TEXT

SEQ ID NO: 7—Description of Artificial Sequence: Synthetic DNA

SEQ ID NO: 8—Description of Artificial Sequence: Synthetic DNA

SEQ ID NO: 9—Description of Artificial Sequence: Synthetic DNA

SEQ ID NO: 10—Description of Artificial Sequence: Synthetic DNA

SEQ ID NO: 11—Description of Artificial Sequence: Synthetic DNA

SEQ ID NO: 12—Description of Artificial Sequence: Synthetic DNA

SEQ ID NO: 13—Description of Artificial Sequence: Synthetic DNA

SEQ ID NO: 14—Description of Artificial Sequence: Synthetic DNA

SEQ ID NO: 15—Description of Artificial Sequence: Synthetic DNA

SEQ ID NO: 16—Description of Artificial Sequence: Synthetic DNA

---

The invention claimed is:

1. A process for producing 7-dehydrocholesterol (hereinafter, "7DHC"), comprising:
    culturing, in a medium, a 7DHC-producing *Labyrinthulea* microorganism in which the 7DHC reducing activity is reduced or lost as compared to a parent strain through deletion, substitution, or addition of at least one base in a gene which is present in the chromosomal DNA of the parent strain and encodes a protein having 7DHC reducing activity;
    allowing 7DHC to be produced and accumulated in the culture; and
    collecting the 7DHC from the culture, wherein
    the gene encoding a protein having 7DHC reducing activity is a gene having any one of DNAs [1] to [5]:
    [1] a DNA encoding a protein having the amino acid sequence shown by SEQ ID NO: 2,
    [2] a DNA encoding a mutated protein consisting of the amino acid sequence of SEQ ID NO: 2 with deletion, substitution, or addition of 1 to 20 amino acids, and having 7DHC reducing activity,
    [3] a DNA encoding a homologous protein having at least 95% identity with the amino acid sequence shown by SEQ ID NO: 2, and having 7DHC reducing activity,
    [4] a DNA that hybridizes with DNA consisting of a base sequence complementary to the base sequence shown by SEQ ID NO: 1 and encodes a homologous protein having 7DHC reducing activity, in which a filter on which a DNA has been immobilized and a probe DNA are incubated overnight at 42° C. in a solution containing 50% formamide, 5×SSC (750 mM sodium chloride and 75 mM sodium citrate), 50 mM sodium phosphate (pH 7.6), 5 ×Denhardt's solution, 10% dextran sulfate, and 20 µg/l of a denatured salmon sperm DNA, and then the filter is washed in a 0.2×SSC solution at about 65° C., and
    [5] a DNA having at least 95% identity with the base sequence shown by SEQ ID NO: 1, and encoding a homologous protein having 7DHC reducing activity.

2. A process for producing vitamin D3, comprising producing 7DHC by the method of claim 1 and irradiating the 7DHC produced with ultraviolet light.

3. The production process according to claim 1, wherein the gene encoding a protein having 7DHC reducing activity has a DNA having the base sequence shown by SEQ ID NO: 1.

4. A process for producing vitamin D3, comprising producing 7DHC by the method of claim 3 and irradiating the 7DHC produced with ultraviolet light.

5. The production process according to claim 1, wherein the *Labyrinthulea* microorganism is a *Labyrinthulea* microorganism of the genus *Schizochytorium, Thraustochytrium, Aurantiochytrium, Parietichytrium, Labyrinthula, Althornia, Aplanochytrium, Japonochytrium, Labyrinthuloides, Ulkenia, Oblongichytrium, Botryochytrium*, or *Sicyoidochytrium*.

6. A process for producing vitamin D3, comprising producing 7DHC by the method of claim 5 and irradiating the 7DHC produced with ultraviolet light.

7. The production process according to claim 5, wherein the gene encoding a protein having 7DHC reducing activity has a DNA having the base sequence shown by SEQ ID NO: 1.

8. A process for producing vitamin D3, comprising producing 7DHC by the method of claim 7 and irradiating the 7DHC produced with ultraviolet light.

* * * * *